US008026054B2

(12) United States Patent
Sharma et al.

(10) Patent No.: US 8,026,054 B2
(45) Date of Patent: Sep. 27, 2011

(54) ANTIBODIES AGAINST CELLS OF FETAL ORIGIN

(75) Inventors: Arun Sharma, Elmwood Park, IL (US); Sherman Elias, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 547 days.

(21) Appl. No.: 11/570,655

(22) PCT Filed: Jun. 13, 2005

(86) PCT No.: PCT/US2005/020884
§ 371 (c)(1),
(2), (4) Date: Sep. 17, 2008

(87) PCT Pub. No.: WO2005/123779
PCT Pub. Date: Dec. 29, 2005

(65) Prior Publication Data
US 2009/0011409 A1    Jan. 8, 2009

Related U.S. Application Data

(60) Provisional application No. 60/579,693, filed on Jun. 14, 2004, provisional application No. 60/618,963, filed on Oct. 15, 2004.

(51) Int. Cl.
*G01N 33/53* (2006.01)
*C12N 5/06* (2006.01)

(52) U.S. Cl. ........................................... 435/6; 435/326

(58) Field of Classification Search ........................ None
See application file for complete search history.

(56) References Cited

U.S. PATENT DOCUMENTS

| 5,580,724 A | 12/1996 | Alter |
| 5,641,628 A | 6/1997 | Bianchi |
| 5,843,633 A | 12/1998 | Yin |
| 5,877,299 A | 3/1999 | Thomas |
| 2004/0005322 A1 | 1/2004 | Kuchroo et al. |

FOREIGN PATENT DOCUMENTS
WO     03063792 A3     8/2003

OTHER PUBLICATIONS

Liang et al. (2001), Immunogenetics 53(5): 357-368.
Ishibashi et al. (2001), Gene 264(1): 87-93.
Bidri et al. (1996), Revue Francaise D'Allergologie et D'Immunologie Clinique 36(8): 859-878. (Translation abstract only).
Zipursky et al. (1959), Lancet 1: 451-452.
Herzenberg et al. (1979), Proc. Natl. Acad. Sci. U. S. A. 76: 1453-1455.
Bianchi et al. (1990), Proc. Natl. Acad. Sci. U. S. A. 87: 3279-3283.
Dubernard G, Oster M, Chareyre F, Antoine M, Rouzier R, Uzan S, Aractingi S, Khosrotehrani K. Increased fetal cell microchimerism in high grade breast carcinomas occurring during pregnancy. Int J Cancer. Mar. 1, 2009;124(5):1054-9.

Zhang L, Wang Y, Liao AH. Quantitative abnormalities of fetal trophoblast cells in maternal circulation in preeclampsia. Prenat Diagn. Dec. 2008;28(12):1160-6.
van Wijk IJ, Griffioen S, Tjoa ML, Mulders MA, van Vugt JM, Loke YW, Oudejans CB. HLA-G expression in trophoblast cells circulating in maternal peripheral blood during early pregnancy. Am J Obstet Gynecol. Apr. 2001;184(5):991-7.
Huang R, Barber TA, Schmidt MA, Tompkins RG, Toner M, Bianchi DW, Kapur R, Flejter WL. A microfluidics approach for the isolation of nucleated red blood cells (NRBCs) from the peripheral blood of pregnant woman. Prenat Diagn. Oct. 2008;28(10):892-9.
D'Souza E, Ghosh K, Colah R. A comparison of the choice of monoclonal antibodies for recovery of fetal cells from maternal blood using FACS for nonivasive prenatal diagnosis of hemoglobinopathies.Cytometry B Clin Cytom. Oct. 2, 2008. [Epub ahead of print].
Engel K, Plonka T, Bilar M, Czajkowska E, Orzińska E, Brojer E, Ronin-Walknowska E. The analysis of the correlation between extracellular fetal DNA concentration in maternal circulation and severity of preeclampsia. Ann Acad Med Stetin. 2007;53(3):20-5.
Huang DJ, Mergenthaler-Gatfield S, Hahn S, Holzgreve W, Zhong XY. Isolation of cell-free DNA from maternal plasma using manual and automated systems. Methods Mol Biol. 2008;444:203-8.
Khosrotehrani K, Leduc M, Bachy V, Nguyen Huu S, Oster M, Abbas A, Uzan S, Aractingi S. Pregnancy allows the transfer and differentiation of fetal lymphoid progenitors into functional T and B cells in mothers. J Immunol. Jan. 15, 2008;180(2):889-97.
Kolialexi A, Vrettou C, Traeger-Synodinos J, Burgemeister R, Papantoniou N, Kanavakis E, Antsaklis A, Mavrou A. Noninvasive prenatal diagnosis of beta-thalassaemia using individual fetal erythroblasts isolated from maternal blood after enrichment. Prenat Diagn. Dec. 2007;27(13):1228-32.
Porra V, Bernaud J, Gueret P, Bricca P, Rigal D, Follea G, Blanchard D. Identification and quantification of fetal red blood cells in maternal blood by a dual-color flow cytometric method: evaluation of the Fetal Cell Count kit. Transfusion. Jul. 2007;47(7):1281-9.
Zhong XY, Hahn S, Steinborn A, Holzgreve W. Quantitative analysis of intact fetal cells in maternal plasma by real-time PCR. Eur J Obstet Gynecol Reprod Biol. Jul. 2007;133(1):20-4.
Sekizawa A, Purwosunu Y, Matsuoka R, Koide K, Okazaki S, Farina A, Saito H, Okai T. Recent advances in non-invasive prenatal DNA diagnosis through analysis of maternal blood. J Obstet Gynaecol Res. Dec. 2007;33(6):747-64.
Mavrou A, Kolialexi A, Souka A, Pilalis A, Kavalakis Y, Antsaklis P, Kanavakis E, Antsaklis A First-trimester NRBC count in maternal circulation: correlation with doppler ultrasound studies J Histochem Cytochem. Mar. 2005;53 (3):315-7.
Sugawara J, Mitsui-Saito M, Hoshiai T, Hayashi C, Kimura Y, Okamura K. Circulating endothelial progenitor cells during human pregnancy. J Clin Endocrinol Metab. Mar. 2005;90(3):1845-8.

(Continued)

*Primary Examiner* — Michail Belyavskyi
(74) *Attorney, Agent, or Firm* — McDonnell Boehnen Hulbert & Berghoff LLP

(57) ABSTRACT

This invention relates to antibodies that specific bind to fetal CD36+ cells in preference to binding to maternal CD36+ cells and methods for using these antibodies to detect and separate fetal cells from adult biological fluids including maternal peripheral blood.

6 Claims, 2 Drawing Sheets

OTHER PUBLICATIONS

Guetta E, Simchen MJ, Mammon-Daviko K, Gordon D, Aviram-Goldring A, Rauchbach N, Barkai G. Analysis of fetal blood cells in the maternal circulation: challenges, ongoing efforts, and potential solutions. Stem Cells Dev. Feb. 2004;13(1):93-9.

Hennerbichler S, Kroisel PM, Zierler H, Pertl B, Wintersteiger R, Dohr G, Sedlmayr P Fetal nucleated red blood cells in peripheral blood of pregnant women: detection and determination of location on a slide using laser-scanning cytometry. Prenat Diagn. Sep. 2003;23(9):710-5.

O'Donoghue K, Choolani M, Chan J, de la Fuente J, Kumar S, Campagnoli C, Bennett PR, Roberts IA, Fisk NM. Identification of fetal mesenchymal stem cells in maternal blood: implications for non-invasive prenatal diagnosis. Mol Hum Reprod. Aug. 2003;9(8):497-502.

Larsen RD, Schønau A, Thisted M, Petersen KH, Lohse J, Christensen B, Philip J, Pluzek KJ. Detection of gamma-globin mRNA in fetal nucleated red blood cells by PNA fluorescence in situ hybridization. Prenat Diagn. Jan. 2003;23 (1):52-9.

Al-Mufti R, Hambley H, Farzaneh F, Nicolaides KH.Fetal erythroblasts in maternal blood in relation to gestational age. Matern Fetal Neonatal Med. Dec. 2003;14(6):392-7.

Al-Mufti R, Hambley H, Farzaneh F, Nicolaides KH. Distribution of fetal and embryonic hemoglobins in fetal erythroblasts enriched from maternal blood.Haematologica. Apr. 2001;86(4):357-62.

Mikhail MA, M'Hamdi H, Welsh J, Levicar N, Marley SB, Nicholls JP, Habib NA, Louis LS, Fisk NM, Gordon MY. High frequency of fetal cells within a primitive stem cell population in maternal blood. Hum Reprod. Apr. 2008;23(4):928-33.

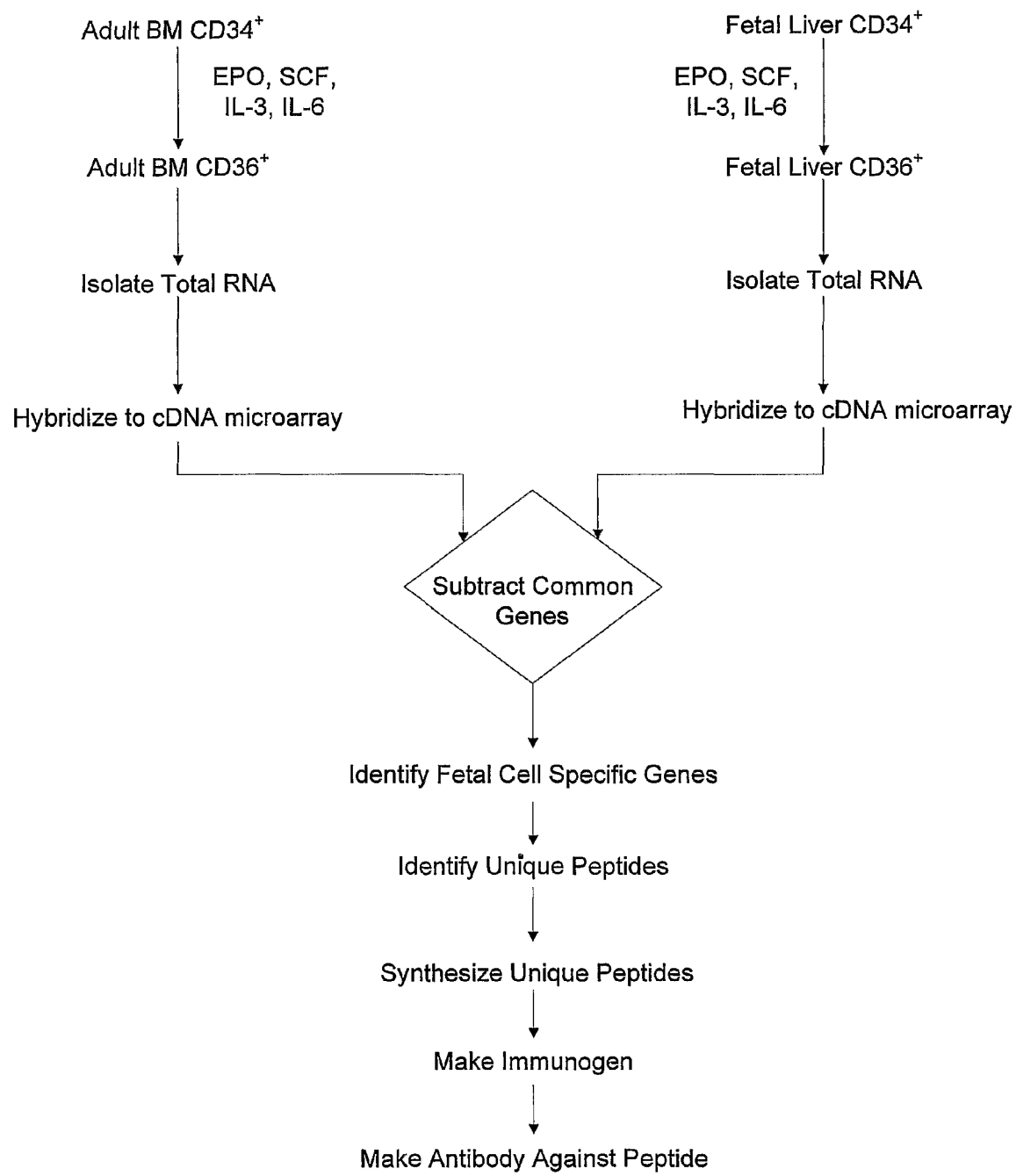

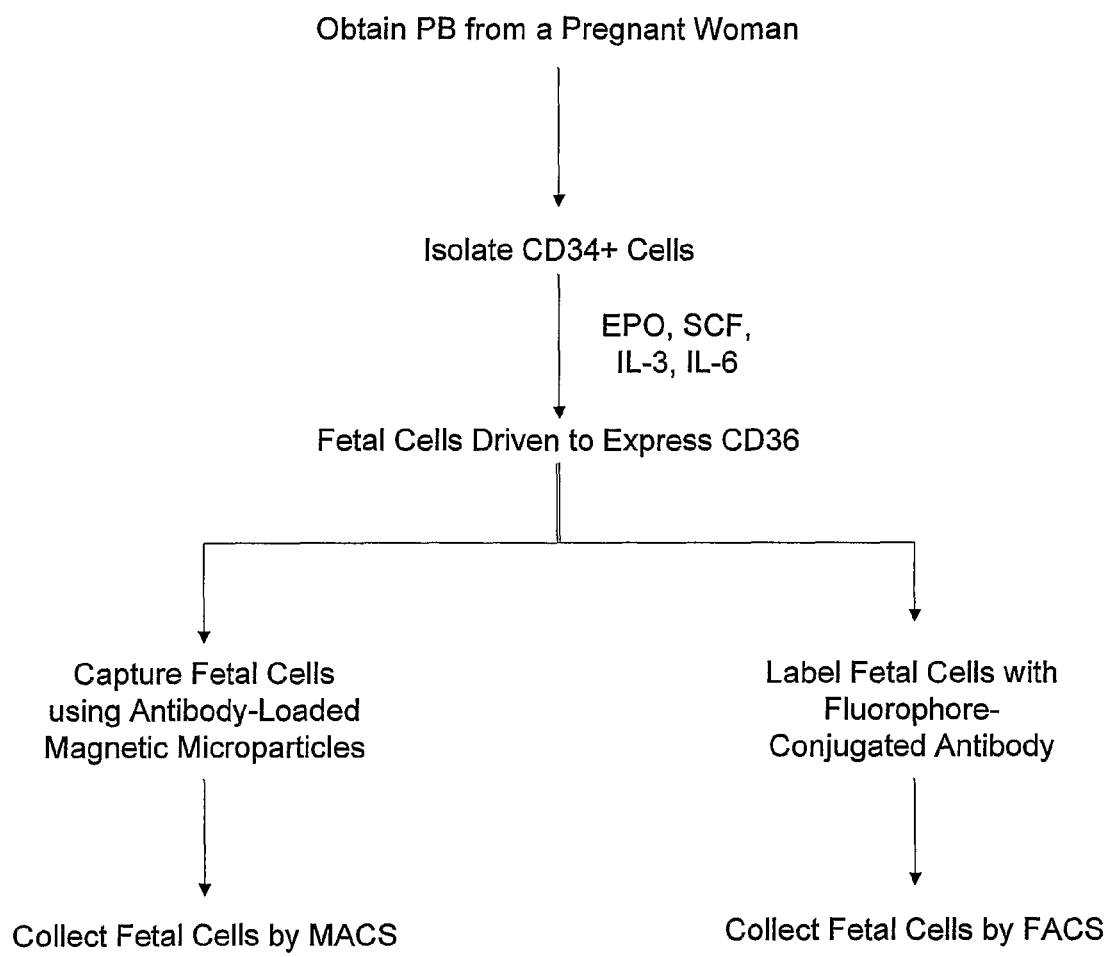
Figure 2: Isolation of Fetal Cells from Maternal Blood

SEQUENCE LISTING

```
<160> NUMBER OF SEQ ID NOS: 28

<210> SEQ ID NO 1
<211> LENGTH: 20
<212> TYPE: PRT
<213> ORGANISM: Artificial
<220> FEATURE:
<223> OTHER INFORMATION: Synthetic peptide

<400> SEQUENCE: 1

Asn Thr Thr Gln Pro Lys Leu Leu Ala Pro His Gln His Glu Lys Ser
1               5                   10                  15

Gln Lys Lys Ser
            20

<210> SEQ ID NO 2
<211> LENGTH: 20
<212> TYPE: PRT
<213> ORGANISM: Artificial
<220> FEATURE:
<223> OTHER INFORMATION: Synthetic peptide

<400> SEQUENCE: 2

Cys Ile Asn Ala Leu Ser Ser Asn Leu Lys Ser Pro Arg Leu Ser Gln
1               5                   10                  15

Pro Ala Glu Glu
            20

<210> SEQ ID NO 3
<211> LENGTH: 20
<212> TYPE: PRT
<213> ORGANISM: Artificial
<220> FEATURE:
<223> OTHER INFORMATION: Synthetic peptide

<400> SEQUENCE: 3

Phe Thr Pro Lys Gly Ile Thr Ile Pro Gln Arg Glu Lys Pro Gly His
1               5                   10                  15

Met Tyr Gln Asn
            20

<210> SEQ ID NO 4
<211> LENGTH: 20
<212> TYPE: PRT
<213> ORGANISM: Artificial
<220> FEATURE:
```

<223> OTHER INFORMATION: Synthetic peptide

<400> SEQUENCE: 4

Tyr Ser Asn Asn Pro Gly Ser Ser Phe Ser Ser Thr Gln Ser Gln Asp
1               5                   10                  15

His Ile Gln Gln
            20

<210> SEQ ID NO 5
<211> LENGTH: 20
<212> TYPE: PRT
<213> ORGANISM: Artificial
<220> FEATURE:
<223> OTHER INFORMATION: Synthetic peptide

<400> SEQUENCE: 5

Phe Ser Gln Ala Glu Lys Pro Glu Pro Thr Asn Gln Gly Gln Asp Ser
1               5                   10                  15

Leu Lys Lys His
            20

<210> SEQ ID NO 6
<211> LENGTH: 20
<212> TYPE: PRT
<213> ORGANISM: Artificial
<220> FEATURE:
<223> OTHER INFORMATION: Synthetic peptide

<400> SEQUENCE: 6

Pro Ala Ser Leu Gln Cys Glu Leu Asp Lys Asn Asn Ile Pro Thr Arg
1               5                   10                  15

Ser Tyr Val Ser
            20

<210> SEQ ID NO 7
<211> LENGTH: 20
<212> TYPE: PRT
<213> ORGANISM: Artificial
<220> FEATURE:
<223> OTHER INFORMATION: Synthetic peptide

<400> SEQUENCE: 7

His Glu Leu Gly Gly Ser Glu Asp Cys Val Glu Val Gln Pro Asp Gly
1               5                   10                  15

Arg Trp Asn Asp
            20

<210> SEQ ID NO 8
<211> LENGTH: 19
<212> TYPE: PRT
<213> ORGANISM: Artificial
<220> FEATURE:
<223> OTHER INFORMATION: Synthetic peptide

<400> SEQUENCE: 8

Leu Gln Val Tyr Arg Trp Val Cys Glu Lys Arg Arg Asn Ala Thr Gly
1               5                   10                  15

Glu Val Ala

<210> SEQ ID NO 9
<211> LENGTH: 20
<212> TYPE: PRT
<213> ORGANISM: Artificial
<220> FEATURE:
<223> OTHER INFORMATION: Synthetic peptide

```
<400> SEQUENCE: 9

Met Asp Ser Ser Thr Ala His Ser Pro Val Phe Leu Val Phe Pro Pro
1               5                   10                  15

Glu Ile Thr Ala
            20

<210> SEQ ID NO 10
<211> LENGTH: 20
<212> TYPE: PRT
<213> ORGANISM: Artificial
<220> FEATURE:
<223> OTHER INFORMATION: Synthetic peptide

<400> SEQUENCE: 10

Thr Phe Gly Phe Ile Leu Asp Gln Asn Tyr Ile Cys Gly Tyr Ser His
1               5                   10                  15

Gln Asn Ser Gln
            20

<210> SEQ ID NO 11
<211> LENGTH: 21
<212> TYPE: PRT
<213> ORGANISM: Artificial
<220> FEATURE:
<223> OTHER INFORMATION: Synthetic peptide

<400> SEQUENCE: 11

Cys Asn Thr Thr Gln Pro Lys Leu Leu Ala Pro His Gln His Glu Lys
1               5                   10                  15

Ser Gln Lys Lys Ser
            20

<210> SEQ ID NO 12
<211> LENGTH: 21
<212> TYPE: PRT
<213> ORGANISM: Artificial
<220> FEATURE:
<223> OTHER INFORMATION: Synthetic peptide

<400> SEQUENCE: 12

Cys Cys Ile Asn Ala Leu Ser Ser Asn Leu Lys Ser Pro Arg Leu Ser
1               5                   10                  15

Gln Pro Ala Glu Glu
            20

<210> SEQ ID NO 13
<211> LENGTH: 21
<212> TYPE: PRT
<213> ORGANISM: Artificial
<220> FEATURE:
<223> OTHER INFORMATION: Synthetic peptide

<400> SEQUENCE: 13

Cys Phe Thr Pro Lys Gly Ile Thr Ile Pro Gln Arg Glu Lys Pro Gly
1               5                   10                  15

His Met Tyr Gln Asn
            20

<210> SEQ ID NO 14
<211> LENGTH: 21
<212> TYPE: PRT
<213> ORGANISM: Artificial
<220> FEATURE:
<223> OTHER INFORMATION: Synthetic peptide
```

-continued

```
<400> SEQUENCE: 14

Cys Phe Thr Pro Lys Gly Ile Thr Ile Pro Gln Arg Glu Lys Pro Gly
1               5                   10                  15

His Met Tyr Gln Asn
            20

<210> SEQ ID NO 15
<211> LENGTH: 21
<212> TYPE: PRT
<213> ORGANISM: Artificial
<220> FEATURE:
<223> OTHER INFORMATION: Synthetic peptide

<400> SEQUENCE: 15

Cys Phe Ser Gln Ala Glu Lys Pro Glu Pro Thr Asn Gln Gly Gln Asp
1               5                   10                  15

Ser Leu Lys Lys His
            20

<210> SEQ ID NO 16
<211> LENGTH: 21
<212> TYPE: PRT
<213> ORGANISM: Artificial
<220> FEATURE:
<223> OTHER INFORMATION: Synthetic peptide

<400> SEQUENCE: 16

Cys Pro Ala Ser Leu Gln Cys Glu Leu Asp Lys Asn Asn Ile Pro Thr
1               5                   10                  15

Arg Ser Tyr Val Ser
            20

<210> SEQ ID NO 17
<211> LENGTH: 22
<212> TYPE: PRT
<213> ORGANISM: Artificial
<220> FEATURE:
<223> OTHER INFORMATION: Synthetic peptide

<400> SEQUENCE: 17

Cys Ala Met Asp Ser Ser Thr Ala His Ser Pro Val Phe Leu Val Phe
1               5                   10                  15

Pro Pro Glu Ile Thr Ala
            20

<210> SEQ ID NO 18
<211> LENGTH: 22
<212> TYPE: PRT
<213> ORGANISM: Artificial
<220> FEATURE:
<223> OTHER INFORMATION: Synthetic peptide

<400> SEQUENCE: 18

Cys Ala Thr Phe Gly Phe Ile Leu Asp Gln Asn Tyr Ile Cys Gly Tyr
1               5                   10                  15

Ser His Gln Asn Ser Gln
            20

<210> SEQ ID NO 19
<211> LENGTH: 21
<212> TYPE: DNA
<213> ORGANISM: Artificial
<220> FEATURE:
<223> OTHER INFORMATION: Synthetic oligonucleotide
```

-continued

<400> SEQUENCE: 19
tcctcaaaag aaaccgtgca t                                              21

<210> SEQ ID NO 20
<211> LENGTH: 26
<212> TYPE: DNA
<213> ORGANISM: Artificial
<220> FEATURE:
<223> OTHER INFORMATION: Synthetic oligonucleotide

<400> SEQUENCE: 20
agattaatgg ttgctaagga ctggat                                         26

<210> SEQ ID NO 21
<211> LENGTH: 21
<212> TYPE: DNA
<213> ORGANISM: Artificial
<220> FEATURE:
<223> OTHER INFORMATION: Synthetic oligonucleotide

<400> SEQUENCE: 21
ccccacacac atgcacttac c                                              21

<210> SEQ ID NO 22
<211> LENGTH: 21
<212> TYPE: DNA
<213> ORGANISM: Artificial
<220> FEATURE:
<223> OTHER INFORMATION: Synthetic oligonucleotide

<400> SEQUENCE: 22
cctagtccca gggctttgat t                                              21

<210> SEQ ID NO 23
<211> LENGTH: 22
<212> TYPE: DNA
<213> ORGANISM: Artificial
<220> FEATURE:
<223> OTHER INFORMATION: Synthetic oligonucleotide

<400> SEQUENCE: 23
gtgcacctga ctcctgagga ga                                             22

<210> SEQ ID NO 24
<211> LENGTH: 21
<212> TYPE: DNA
<213> ORGANISM: Artificial
<220> FEATURE:
<223> OTHER INFORMATION: Synthetic oligonucleotide

<400> SEQUENCE: 24
ccttgatacc aacctgccca g                                              21

<210> SEQ ID NO 25
<211> LENGTH: 26
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (26)..(26)
<223> OTHER INFORMATION: 3'-TAMRA

```
<400> SEQUENCE: 25
aaggtgaacg tggatgaagt tggtgg                                          26

<210> SEQ ID NO 26
<211> LENGTH: 21
<212> TYPE: DNA
<213> ORGANISM: Artificial
<220> FEATURE:
<223> OTHER INFORMATION: Synthetic oligonucleotide

<400> SEQUENCE: 26
tggcgattaa gtcaaattcg c                                               21

<210> SEQ ID NO 27
<211> LENGTH: 25
<212> TYPE: DNA
<213> ORGANISM: Artificial
<220> FEATURE:
<223> OTHER INFORMATION: Synthetic oligonucleotide

<400> SEQUENCE: 27 cccctagta ccctgacaat gtatt                                            25

<210> SEQ ID NO 28
<211> LENGTH: 26
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-FAM
<220> FEATURE:
<221> NAME/KEY: misc_feature
<222> LOCATION: (26)..(26)
<223> OTHER INFORMATION: 3'-TAMRA

<400> SEQUENCE: 28
agcagtagag cagtcaggga ggcaga                                          26
```

ANTIBODIES AGAINST CELLS OF FETAL ORIGIN

This application claims priority to U.S. Ser. No. 60/579,693, filed Jun. 14, 2004 and U.S. Ser. No. 60/618,963, filed Oct. 15, 2004, the teachings of each of which are explicitly incorporated by reference herein.

FIELD OF THE INVENTION

This invention relates to antibodies that bind to fetal CD36+ cells in preference to binding maternal CD36+ cells and the use of these antibodies for detecting and separating fetal cells from maternal peripheral blood.

DESCRIPTION OF RELATED ART

The presence of fetal red blood cells in maternal blood immediately after delivery was first reported by Zipursky et al. in 1959 ("Foetal erythrocytes in the maternal circulation," Lancet 1:451-52). It was subsequently demonstrated that fetal red cells, lymphocytes and trophoblasts cells are present in maternal blood during pregnancy. (Herzenberg et al, 1979, Proc Natl Acad Sci USA. 76: 1453-1455; Bianchi et al., 1990, Proc Nat Acad Sci USA. 87:3279-83) It has been widely recognized that the presence of fetal cells in maternal blood provides an opportunity to obtain fetal cell samples for clinical diagnostic testing and for research purposes at minimum risk to the fetus. This contrasts to currently widely used methods of obtaining fetal cell samples such as chorionic villus sampling (CVS), amniocentesis, or periumbilical blood sampling (PUBS). While effective and widely used, these methods are directly invasive to the fetus and can increase risk of fetal morbidity or mortality, including miscarriage. The usefulness of obtaining fetal cells from maternal blood is, however, limited by the low numbers of fetal cells that are present in the peripheral blood of the mother. The reported ratios of fetal to maternal erythroid cells are generally in the range of 1:4,000 to 1:80,000. The corresponding reported ratios for lymphocytes are considerably more variable, ranging from 1:100 to 1:300,000 depending upon multiple factors including the specific analytical method used and the gestational age of the fetus.

Numerous methods for recovering fetal cells from maternal blood have been proposed. One group of such methods, exemplified by U.S. Pat. No. 5,641,628 and incorporated herein by reference, proposes using fetal cell-specific monoclonal antibodies, particularly anti-CD71 (transferrin receptor) to bind to fetal erythroid cells. Others have employed antibodies specific for cell surface antigens such as CD34 and glycophorin A for similar purposes. Certain commonly practiced embodiments of this approach employ antibodies that have been conjugated to a detectable moiety such as a fluorophore. Conjugated antibody binding to a fetal cell permits these cells to be detected in the presence of other cells that do not display the cognate antigen. This detection is sometimes used in conjunction with fluorescence activated cell sorting (FACS) instrumentation to permit labeled fetal cells to be separated from the commingled unlabeled maternal cells. In other common embodiments of this approach, fetal cell-specific antibodies are attached to a solid surface or magnetic microparticle and use the immobilized antibody to capture fetal cells. Antibody binding to the target fetal cells attaches them to a supporting surface, microparticle, microporous filter, porous insoluble matrix or other such entity while the maternal cells are not bound and will, therefore, remain in the liquid phase. The supporting entity with bound fetal cells can then be readily separated from the maternal cell-containing liquid phase. Both classes of fetal cell-separating methods are based upon and utilize accepted methods and materials that are well established in the art for this and other related purposes. These approaches are limited by the aforementioned rarity of fetal cells in maternal blood, as well as the developmental biology of hematopoietic and fetal stem cells.

Detecting fetal cells in maternal blood using the methods described above is an exercise in "rare event" detection. Performance of these direct immunological methods is difficult to accurately assess from most published data because, inter alia, typical metrics are reported as the "yield of pure product" or "sensitivity" and "specificity"; or the data to compute such metrics are frequently not reported at all. It is more common for labeled or, if appropriate, recovered cell counts to be reported without further determination or reporting of either false negatives or false positives contained therein. Crude estimates of performance, however, can be derived based upon the total cell count in the sample and an estimated frequency of occurrence of the cell type(s) of interest in the sample. By way of example, assuming that it is reported that a sample contains $1 \times 10^7$ total cells and that the frequency of occurrence of the target cells in the sample is 1:25,000 (both values being realistic for experiments in which fetal erythroid cells are labeled in or recovered from maternal blood), it can reasonably be anticipated that there will be approximately 40 fetal cells in the sample. If the reported number of cells that are labeled or recovered using the method being described is substantially less than this anticipated value, the sensitivity of the method, i.e., the ratio or percentage of the fetal cells actually present in a sample that are detected by the method, can be considered low. Conversely, if the reported number of cells that are labeled or recovered using the described method is substantially greater than this anticipated value, the specificity of the method, i.e., the ratio or percentage of the cells detected by the method that are actually fetal cells, is low. Applying this type of meta-analysis to published experimental results for the labeling or recovery of erythroid fetal cells from maternal blood often yields an imputed value of sensitivity or specificity (as appropriate) of less than 25% and occasionally less than 10%.

These imputed sensitivities and specificities for direct immunological labeling or capture of fetal cells can be put into perspective by considering the results reported for the closely analogous application of immunochemical screening of cervical cytology specimens for the presence of dysplastic and cancerous cells. Like fetal cell detection, cervical cytology screening is an exercise in rare event detection in which the frequency of occurrence of cells of interest is often in the 1:10,000 to 1:50,000 range. Similarly, some of the same antibodies, most notably an antibody specific for CD71, are used in some implementations of both applications. The methods employed in performing the labeling of the sample, for capturing the data; and interpreting these results is likewise very similar. Sensitivities and specificities are, however, routinely reported for the cervical cytology results typically fall within the 85% to 95% range. This comparison strongly suggests that both the sensitivity and specificity of methods for direct immunological labeling or capture of fetal cells in or from a sample of maternal blood is inadequate.

Numerous attempts have been made to improve the sensitivity and specificity of fetal cell labeling and/or recovery from maternal blood. These improvements have taken the form of enriching the specimen in fetal cells prior to performing the final labeling or capture steps. Virtually all practitioners of this art, for example, sediment the maternal blood sample through a Ficoll or similar density gradient before performing any operations that are fetal cell-specific. This sedimentation process permits a maternal blood specimen to be separated into three major fractions: erythrocytes, mononuclear cells and platelets. The erythrocyte and platelet fractions together account for the vast majority of the cells present in the original sample, while the mononuclear fraction contains the fetal cells of interest. Removing the bulk of the potentially interfering cells from the sample non-specifically enriches for target fetal cells and improves the likelihood that these cells will be labeled or captured. However, most current separation methods, including the ones discussed in the preceding paragraph, employ such enrichment methods, indicating that enrichment is not sufficient to remedy the deficiencies in specificity and sensitivity known in these prior art methods.

Consequently, the mononuclear fraction has been further enriched by some workers. One commonly-employed method (see, for example, U.S. Pat. No. 5,641,628) selectively isolates cells from the monocyte fraction that display cell surface antigens associated with fetal cells. Conversely, cells that do not display fetal cell-associated antigens can be removed (subtracted) from the mixture (this is illustrated in U.S. Pat. No. 5,877,299). Such selective isolation of fetal cells typically uses antibodies specific for early stage fetal cell markers such as CD34 and/or CD133, used either alone or in combination. The subtractive approach typically uses "cocktails" containing multiple antibodies, each of which is specific for a particular type of cell to be removed from the mixture. The mechanics of such separations are generally as described above and are based upon established methods such as FACS, magnetic separation, affinity chromatography or cell panning.

The primary limitation on the efficacy of this approach is a consequence of the process of cell development. All cells derive from pluripotent stem cells that have the potential to differentiate to form virtually any cell that is found in an organism. Pluripotent stem cells are the predominant cell type in very early stage embryos, but decline rapidly in number to the point of undetectability as the embryo develops. During development the ability of these pluripotent stem cells to differentiate is progressively reduced as these cells become committed to the formation of specific organs and tissues. The initial restriction on differentiation results in the formation of classes of multi-potent stem cells, each class being capable of giving rise to all cell types within a particular broad range. Hematopoietic stem cells, for example, can give rise to any of the blood cell types. These stem cells have considerable proliferative potential and exhibit the properties of self-renewal, engraftment and, when appropriately stimulated, differentiation into "progenitor" stem cells. These progenitor cells retain the proliferative and engraftment capacities of the parent multipotent stem cells, but are restricted to differentiation into cells of a specific hematopoietic lineage. Whereas, for example, hematopoietic stem cells can give rise to cells of the erythroid, myeloid, megakaryocytic, lymphoid, and, possibly, veto lineages of blood cells, a progenitor cell derived from a hematopoietic stem cell is committed to differentiating into the cells of just one of these lineages (i.e., erythroid, myeloid, megakaryocytic, etc.). Like pluripotent and multipotent stem cells, progenitor cells are not distinguishable on the basis of morphology, but rather are recognized by their progeny. When suitably stimulated, these progenitor cells undergo additional rounds of differentiation leading to the penultimate differentiated cell within the particular progression. Within the erythroid lineage, for example, an early stage of differentiation presents as a "burst forming unit-erythroid" (BFU-E) and later presents as a "colony forming unit-erythroid" (CFU-E) before progressing to the morphologically identifiable erythroblast "precursor" cells. These precursor cells further progressively differentiate through the proerythroblast, basophilic, polychromatophilic, and orthochromatic erythroblasts stages before enucleating to become reticulocytes and ultimately erythrocytes.

This progression of changes resulting from differentiation is reflected in changes in the cell surface antigens that are presented by the cell. Within the erythroid progression, for example, hematopoietic stem cells and BFU-E cells express CD34 and 17F11 (c-kit) while CD33 is expressed during the BFU-E stage, but none of these antigens are expressed during the CFU-E or later stages. CD71 (transferrin receptor, TFR) appears in the late BFU-E or early CFU-E stage and persists through the reticulocyte stage, while CD36 (thrombospondin receptor, TSPR) appears late in the CFU-E stage and persists even in some mature erythrocytes. Glycophorin A and the Blood Group A antigen appear at the erythroblast stage and persist into mature erythrocytes. Other antigens show similar changes in expression as a function of the stage of differentiation.

This variability in expression is one limitation on using these antigens for separating fetal cells from non-fetal cells. Using CD34, for example, identifies cells at the hematopoietic stem cell and BFU-E stages, but does not identify any of the later progeny. Conversely, CD71 does not identify cells at the hematopoietic stem cell and BFU-E stages, but does identify later stage cells. Thus a combination of CD34 and CD71 antibodies would need to be employed in order to ensure that all of the cells of interest are labeled and/or captured in order to avoid a significant loss in sensitivity. A similar situation applies to "subtractive" methods of sample enrichment because they require antibodies that bind to all of the undesired cell types in all of their developmental stages without binding to fetal cells.

A further limitation on existing methods of fetal cell separation is that many of these antigens appear on multiple, often unrelated cell types. CD71, for example, is intimately involved in iron metabolism and is therefore expressed by virtually all actively respiring mammalian cells. Similarly, CD36 is involved in cell adhesion and certain regulatory functions and is expressed by a variety of blood and other cell types. This expression of antigens across broad ranges of cell types impairs the specificity of methods dependent on these antigens. In addition, expression of certain of these cell surface markers is dependent not only on cell type and developmental stage but on a variety of other, environmental factors that reduce the usefulness of these antigens as differentiation markers. CD71, for example, is under tight transcriptional, translational and post-translational regulation. Expression of CD71 is controlled not only by the stage of development of the cell, but also by numerous environmental factors. This environmental sensitivity can reduce the method's, sensitivity, specificity or both. Finally, fetal and maternal blood cells of the same type and development stage express essentially the same antigens, making it difficult to distinguish the origin of any particular cell. Under certain circumstances, this type of limitation can be overcome: fetal erythroblasts express fetal hemoglobin while the maternal erythroblasts express the adult form, for example, and the paternal Y chromosome can be detected in cells from male fetuses.

In light of these limitations, other methods have been developed for selectively enriching the fetal cell component of maternal blood samples. One approach, disclosed in U.S. Pat. No. 5,580,724, uses the higher proliferative capability of fetal cells compared with maternal cells of the same cell type. In this method, CD34$^+$ cells are collected from the maternal blood sample in accordance with one of the methods outlined above and then expanded in cell culture in the presence of the appropriate cytokines and other factors. As fetal CD34+ cells have a higher proliferative capability than do maternal CD34+ cells, expansion through multiple cycles of cell division progressively increases the proportion of early stage fetal cells in the culture. As the combination of cytokines and other factors used to promote this selective expansion are largely specific for the promotion of proliferation but not differentiation of CD34+ cells, the population of later stage fetal cells is not expanded to a similar degree.

U.S. Pat. No. 5,843,633 discloses yet another approach, in which intact fetal cells or stem cells are used as immunogens for preparing monoclonal antibodies. This method results in a complex mixture of hybridomas each of which expresses an antibody that is directed against one of the panoply of antigenic epitopes that are displayed by fetal or stem cells. These hybridomas are typically purified into clones each expressing a single antibody that is then individually screened against panels of fetal and other cell types to determine which, if any, of these antibodies exhibits useful levels of specificity for fetal cells. In order to adequately assess antibody specificity, the screening panels must include pure specimens of the target fetal or stem cell type(s) as well as specimens of all of contaminating cell types that may be present in a clinical sample. Hybridomas of sufficient specification are then expanded to produce larger quantities of the selected antibody. While such methods have the potential to have sufficient specificity, they are limited by the exhaustive screening that is required in order to identify antibodies exhibiting adequate specificity for fetal or stem cells.

Additional fetal cell-specific antigens have been discovered by comparing proteins or genes expressed by fetal cells proteins or genes expressed by maternal cells to identify those proteins or genes that are strongly expressed in fetal cells, but not in maternal cells. The quality of the comparisons obtained by this method is sensitive to the purities of the maternal and fetal cells used as specimens and to the stringent procedural control required in order to obtain reproducible results. These experiments have been performed using various microarrays having signal-to-noise ratios sufficiently low that significant numbers of replicates must be run in order to obtain useful results. The genetic diversity of each sample and the "coverage" of the array in terms of the percentage of the total possible number of targets actually represented in the array are also significant considerations. A particular limitation is that the maternal and fetal cells of interest for the present purpose are primarily stem cells and cells at the BFU and CFU stages of differentiation. These cells are not recognizable by morphological criteria, but rather are recognized only through their progeny. This introduces significant uncertainty as to the identities of the cells used in this procedure. In any case, once the antigen(s) that is/are uniquely expressed by fetal cells is/are identified, the corresponding proteins can be obtained and antibodies raised against these proteins in accordance with standard methods.

There thus remains in the art a need for more specific and sensitive methods for identifying markers that can distinguish fetal cells from maternal cells, markers useful in such methods, and reagents particularly antibodies for detecting such markers.

SUMMARY OF THE INVENTION

The present invention provides antibodies that preferentially bind to fetal cells rather than maternal cells, methods for preparing such antibodies and methods for using these antibodies to detect and separate fetal cells from other cell types.

A particular and advantageous application of the methods and antibodies of this invention is to specifically label fetal cells and separate such cells from other cell types, particularly maternal cells. Fetal cells isolated using the inventive antibodies and methods are useful for fetal genetic analysis for detecting or diagnosing disease states or for determining fetal gender, and may find further utility in cell-based therapies.

The present invention advantageously differs from existing methods for labeling or capturing fetal cells from maternal blood because, inter alia, it forces fetal cells present in a sample into a pre-defined state prior to labeling or capture, thus allowing the entire population of fetal cells that is present to be labeled or captured by the antibodies of the invention. By way of example, antibodies against cell surface-specific antigens CD34 and CD133 that are widely used separately or in combination predominantly label or capture erythroid fetal cells that are at the CFU-E or earlier stage of differentiation, but do not label or capture erythroid fetal cells at later stages of differentiation. This reduces the yield of fetal cells that can be obtained from a maternal peripheral blood sample. Furthermore, this yield depends upon the degree of differentiation that has happened to occur in the fetal cells in the sample. Forcing all of the fetal cells into a pre-defined state and employing antibodies that are specific for unique antigens that are expressed by fetal cells in this state permits a higher percentage of the fetal cells in a sample to be labeled or captured in a consistent manner.

The methods of the invention are also advantageous because they permit fetal cell samples to be obtained using minimally invasive methods without posing risks to the fetus.

Specific preferred embodiments of the invention will become evident from the following more detailed description of certain preferred embodiments and the claims.

BRIEF DESCRIPTION OF THE FIGURES

FIG. 1 shows a schematic flow chart for the preparation of fetal cell specific antibodies FIG. 2 shows a schematic flow chart for the use of fetal cell antibodies in the separation of fetal cells from maternal peripheral blood.

DETAILED DESCRIPTION OF THE INVENTION

Antibodies provided according to this invention were prepared against peptide antigens that were chosen based upon a systematic investigation of differences in gene expression between fetal and maternal cells when said cells are forced into a pre-defined state. The samples employed in these investigations consisted of separate pools of CD34+ cells (hematopoietic stem cells and erythroid progenitor cells) of fetal and maternal origin. These pools of cells were separately expanded in the presence of the appropriate cytokines and other factors to increase the numbers of CD34+ cells present in the pools. These expanded pools of CD34+ cells were then separately expanded in the presence of certain cytokines and other factors that promote the differentiation of the CD34+ cells to form cells that express CD36, but not CD34.

The total RNA from these pools of fetal and mobilized adult CD36+ cells origin was then separately extracted and transcribed into the corresponding cDNA preparations that were, in turn, hybridized to "expression" or "EST" microarrays from which the genes or ESTs that are uniquely expressed by CD36+ cells of fetal origin can be determined. The amino acid sequences of the proteins that were encoded by these uniquely expressed fetal genes were then determined and evaluated to identify shorter sequences of amino acid residues (typically 10-30 residues) that are unique to the fetal proteins and were not found in any of the gene products (proteins) expressed by CD36+ cells of maternal origin under the same conditions. These unique fetal peptides were synthesized; conjugated (if necessary or advantageous for antigenicity) to a carrier such as Keyhole Limpet Hemocyanin; and used as immunogens for preparing monoclonal or polyclonal antibodies that bind specifically to these unique fetal peptides. These fetal-specific antibodies were then conjugated to a detectable label such as a fluorophore or immobilized on an insoluble support such as a magnetic microparticle, depending upon whether the antibody is to be used for labeling fetal cells or capturing fetal cells from maternal peripheral blood samples.

The antibodies of the present invention can be used to recover erythroid cells of fetal origin from samples of maternal peripheral blood, and thus the invention provides methods therefor. In these methods of the invention, the $CD34^+$ cell fraction is isolated from maternal peripheral blood in accordance with conventional blood cell separation methods and expanded in the presence of the appropriate cytokines and other factors to force differentiation of the $CD34^+$ cells into cells that express CD36 rather than CD34. If the resulting CD36+ cells are to be identified in the sample, for example, by fluorescence microscopy or are to be separated from the sample, for example, by fluorescence-activated cell sorting (FACS), the sample is treated with one or more of the antibodies of this invention that have been conjugated to a detectable label such as a fluorophore. If the resulting CD36+ cells are to be directly captured from the sample, for example, by magnetic separation, cell panning or affinity chromatography, the sample is treated with one or more of the antibodies of this invention that have been immobilized on an insoluble support of a type that is appropriate to the intended separation method.

Cells that have been labeled as set forth in the preceding paragraph can be evaluated microscopically or further analyzed for fetal gender, genetic abnormalities and disease states by in-situ methods such as fluorescence in-situ hybridization (FISH) or reacted with other antibodies or probes and analyzed by flow cytometry. Cells that have been captured in accordance with the methods of the preceding paragraph can be further analyzed for fetal gender, genetic abnormalities and disease states by methods such as FISH, polymerase chain reaction (PCR), karyotyping, or similar methods or they can be used for research or possibly therapeutic purposes.

As disclosed herein, the inventive methods provide for isolation of fetal cells from a variety of biological fluids, including but not limited to peripheral blood, plasma or serum thereof, and saliva.

The present invention provides minimally invasive methods for detecting and capturing cells of fetal origin from maternal peripheral blood. Due to the rarity of fetal cells in an adult biological fluid such as maternal blood, the methods of this invention include the step of removing more numerous maternal cells from a biological fluid, for example maternal erythrocytes and platelets from a maternal blood specimen, using well-established techniques for sedimenting the specimen through a step-format density gradient using Ficoll or an equivalent material as the denser medium. This process results in the erythrocytes being pelleted at the bottom of a centrifuge tube while the platelets remain in the supernatant fluid. The mono-nucleated cells, including the fetal cells of interest, are concentrated at the boundary between the more and less dense media forming the gradient and can be recovered in relatively pure form.

Using a maternal blood sample, the mono-nucleated cell fraction obtained by density gradient sedimentation consists of a mixture of small numbers of cells of fetal origin and maternally derived hematopoietic stem cells, progenitor cells and precursor cells commingled with a large number of mature adult cells. The fetal cells and immature cells of maternal origin can be differentiated from the mature adult cells on the basis of the cell surface antigens (markers) that are displayed by the cells. In particular, existing methods rely on antibodies that specifically bind to the CD34, CD133 and/or similar antigens expressed by immature cells to permit the immature cells of fetal and maternal origin to be separated from the mature cells of maternal origin. Although the CD34, CD133 and similar antigens are not strictly unique to immature blood cells, the other cell types that are known to express these antigens, including small vessel endothelial cells, embryonic fibroblasts, developing epithelial cells and certain types of nerve cells, are unlikely to be present in significant numbers in a properly drawn specimen of maternal blood.

Two general methods are routinely employed for the initial separation of immature blood cells of fetal and maternal origin (hereafter called $CD34^+$ cells) from mature blood cells. One of these methods, fluorescence activated cell sorting (FACS), relies upon selective detection of the immature cells of interest by "labeling" these cells using antibodies that have been conjugated to a fluorescent reporter moiety and that specifically bind to antigens such as CD34 that are expressed by the immature cells. In this method, the mono-nucleated cell fraction obtained by density gradient sedimentation is treated with one or more appropriate fluorescently conjugated antibodies and processed by FACS, which individually examines and classifies each cell based upon fluorescence intensity, forward scatter and side scatter. FACS diverts individual cells that meet pre-determined fluorescent intensity, forward scatter and side scatter criteria (specific for immature cells) into a collection vessel. The cells collected in this vessel are presumptively the desired immature cells of fetal and maternal origin.

Alternative methods can be used for this initial separation of immature blood cells of fetal and maternal origin from mature blood cells. These include methods using antigen-specific antibodies to specifically immobilize cells of interest onto an insoluble support that can readily be separated from the mixture being resolved. Numerous variations of this approach can be practiced in the collection of fetal cells from maternal blood. For example, antibodies specific for CD34, CD133 or similar markers of immature cells are immobilized on the surfaces of magnetic microparticles. When combined with the mono-nucleated cell fraction obtained by density gradient sedimentation, these antibodies bind to their corresponding antigens thereby capturing the cells that display these antigens on the surfaces of the magnetic microparticles. Application of a strong magnetic field causes these magnetic microparticles with captured cells to be held against the sides of the column or container in which this process is being performed, thus allowing the cells that do not display these antigens and, therefore, are not bound to magnetic microparticles, to be eluted. The microparticle-bound cells can then be released from the microparticles and collected as a fraction that is substantially enriched in the cells of interest. Another example of these methods selectively depletes the sample of mature cells in an initial separation and subsequently captures the immature cells as described. This initial depletion of mature cells, which is sometimes referred to as "negative selection", is generally regarded as improving the capture efficacy in the second step. The capture antibodies employed for depleting mature cells are specific for antigens that are specifically expressed by mature cells and are often used as "cocktails" containing multiple antibodies, each of which is specific for a different mature cell marker.

The cell fractions obtained using antibodies specific for CD34 and/or other antigens expressed by immature cells consist of mixtures containing predominantly immature cells of both fetal and maternal origin. Such mixtures are the end products of many of the methods that have been published and/or patented for the recovery of fetal cells from maternal blood. These mixtures have limited utility for diagnostic applications, such as in those cases where the fetus is male and the fetal cells in the mixture can be identified by detection of the presence of a Y-chromosome, and in some therapeutic applications where the substantial engraftment and proliferative capabilities of $CD34^+$ cells are beneficial. Other applications, however, require that the sample be further enriched in cells of fetal origin relative to those of maternal origin.

It has been demonstrated that the proliferative capacity of $CD34^+$ cells of fetal origin are substantially greater than those of $CD34^+$ cells of maternal origin. This difference in proliferative capacity can be employed to differentially enrich the fetal component of these samples by expanding the cells of the sample in the presence of cytokines and other factors that promote the proliferation of $CD34^+$ cells. Under such conditions, the percentage of $CD34^+$ cells of fetal origin in the sample is increased in each cell division cycle thus enriching the sample in $CD34^+$ cells of fetal origin.

These fetal cell-enriched cell populations are inadequate for many diagnostic procedures, which are best performed using samples consisting almost entirely of cells of fetal origin. Attempts to achieve this end have largely focused upon identifying antigens that differentiate between fetal and maternal CD34+ cells, preparing antibodies that specifically bind to these antigens; and using these antibodies in separation procedures as described above. These antigens have been identified and/or antibodies against unidentified fetal cell-specific antigens prepared using empirical methods. For example, antibodies specific for known cellular antigens are screened against panels of nominally pure fetal and maternal cells, often prepared in accordance with the methods described above, to identify those antibodies that apparently preferentially bind to fetal cells. Alternatively, a host animal such as a mouse can be immunized with nominally purified fetal cells as an immunogen, and hybridomas prepared from the resulting immune cells. These hybridomas are the subcloned to homogeneity, for example, by limiting dilution and screening the antibodies produced by these hybridomas against panels of nominally purified fetal and maternal cells prepared as previously described. These methods can in theory produce antibodies useful for specific detection and/or capture of fetal cells from maternal blood. However, the functional quality of these antibodies is critically dependent upon the purity and homogeneity of the immunogen used to produce them, the comprehensiveness of the fetal and maternal cell panels employed for antibody screening, and the purity and homogeneity of the members of these panels, defects in any of which can limit the usefulness of these antibodies. This is a particular problem with regard to the fetal and maternal cells used to produce these antibodies, which are enriched for fetal cells but are not pure preparations thereof. Furthermore, even if the cells used are purely of fetal or maternal origin, these preparations consist of mixtures of cells at different stages of differentiation that display differing constellations of antigens. Thus antibodies prepared according to these methods will, at best, recognize only a subset of the fetal cells that are present in a sample.

These limitations in the art for preparing fetal cell-specific antibodies is addressed by the present invention. Rather than using antibodies to cross-specific cell surface markers, antigen discovery was performed using pooled $CD34^+$ cells prepared as described above. Two separate cell pools were prepared, one from maternal peripheral blood from a non-pregnant donor and the other from fetal liver. The first pool thus consisted of $CD34^+$ cells solely of maternal origin while the second consisted of $CD34^+$ cells solely of fetal origin. Each pool of cells was then separately expanded in the presence of cytokines and other factors that promoted proliferation but not differentiation of $CD34^+$ cells. After optional repurification of these expanded pools, they were expanded a second time in the presence of cytokines and other factors that promoted the differentiation of CD34+ cells to a stage that expresses CD36 antigen but not CD34 antigen and promoted proliferation of $CD36^+$ cells. In addition to increasing the numbers of cells available, this forced shift in cell phenotype reduced the percentage of the pools that consisted of cells that could not differentiate to a CD36-expressing state and collapsed the multiple $CD34^+$ phenotypes that can so differentiate into a smaller number of phenotypes that expressed consistent levels of CD36. Positive or negative selection can be used to further purify these $CD36^+$ pools if desired. This process yielded defined pure preparations of cells of maternal and fetal origin.

The proteins expressed by these viable, purified adult and fetal cell preparations were determined by extracting the total RNA from the cells of each preparation; synthesizing the corresponding labeled cDNA mixtures from this RNA; hybridizing these cDNA mixtures to separate, but identical "gene array" chips; and determining the amount of cDNA binding to each of the probes in the gene arrays in accordance with standard procedures known to those skilled in the art. These data were then evaluated to identify those genes that were strongly expressed by $CD36^+$ fetal cells, but not significantly expressed by $CD36^+$ maternal cells. A decision threshold (Wilcoxon Signed Rank Test p-value of >0.99, more preferably >0.999, even more preferably >0.9999) was typically employed in making these determinations (as disclosed in "Genechip Expression Analysis Technical Manual, PN701024 Rev 3, 2004, Affymetrix Santa Clara Calif.).

The amino acid sequence of the protein product of each gene determined to be uniquely expressed by $CD36^+$ cells of fetal origin, and the amino acid sequences of all proteins significantly expressed by maternal $CD36^+$ cells were determined, typically by reference to standard databases of such information such as Gene Bank and SwissProt. The amino acid sequences of these proteins were then searched to identify amino acid sub-sequences, typically of between 10 and 30 amino acid residues in length, that appeared in proteins of fetal origin but not in proteins of maternal origin. The peptides identified in this manner were taken to be unique markers for $CD36^+$ fetal cells. These unique peptides were chemically synthesized and antibodies raised against these peptides in accordance with conventional techniques. In some cases it was desirable to modify the peptide through the addition of a N-terminal cysteine residue or a C-terminal cysteinyl-alanine dipeptide in order to facilitate preparation of the corresponding immunogen. The resulting antibodies were screened against purified $CD36^+$ cells of fetal and maternal origins to verify their specificity for binding to fetal cells. These antibodies were conjugated to fluorophores for use in FACS analysis and/or separation, or conjugated to magnetic microparticles for use in the magnetic recovery of fetal cells as needed. This procedure identified both extracellular and intracellular protein antigens that are unique to $CD36^+$ fetal cells. Antibodies against the extracellular antigens can be used to capture CD36+ fetal cells; in FACS methods where it is desirable to detect and/or collect viable CD36+ fetal cells; and in microscopic methods where it is desirable to detect and/or collect CD36+ fetal cells independent of viability. Intracellular antigens, on the other hand, are useful for detecting and/or collecting CD36+ fetal cells using FACS methods where cell viability is not a concern and in microscopic methods where it is desirable to detect CD36+ fetal cells.

As provided herein, the antibodies of the invention specifically bind to epitopes comprising peptide fragments of cell surface proteins expressed by fetal cells. Preferably, the epitopes comprising these peptides are available for immunological binding by the antibodies of the invention on the cell surface, most preferably the exterior cell surface, of fetal cells. Preferably, the antibodies are capable of immunologically specific binding to cell surface antigens on fetal cells preferentially to binding on maternal cells, due inter alia to greater expression of the antigen on the fetal cell surface; better conformational arrangement of the antigenic protein on the fetal cell surface; or presence on the fetal cell surface and absence on the maternal cell surface.

As used herein, the term "preferentially bind" or "preferential binding" will be understood to mean that the antibodies and fragments thereof provided by the invention, as well as mixtures of such antibodies or antibody fragments, bind to fetal cells with an affinity or avidity that is about 5 to about 200-fold, more preferably 10- to 100-fold, and even more preferably 20- to 50-fold higher than said antibodies and fragments thereof bind to maternal cells.

It will be further understood by those with skill in the art that the antibodies and fragments thereof provided by the invention include antisera, purified polyclonal antibodies and fragments thereof, as well as mixtures thereof, provided alone or in combination, and further can comprise antibodies or antisera raised by conventional methods using purified fetal cells, and more preferably antigenic peptides obtained from said cells, and even more preferably peptide antigens produced by in vitro chemical or other synthetic routes and used as an immunogen according to conventional methods. In particular, the invention also comprises monoclonal antibodies and fragments thereof, and more particularly combinations of a plurality of said monoclonal antibodies. Said antibodies can be produced according to the methods set forth herein, or antibodies raised by any method to be immunologically reactive with an antigen expressed preferentially on a fetal cell.

These antibodies can be advantageously employed for recovering hematopoietic cells of fetal origin from maternal peripheral blood. These embodiments of the inventive methods are practiced by obtaining a sample of peripheral blood from a pregnant mother; isolating the mononuclear cell fraction from this blood sample; collecting the CD34+ sub-fraction of these mononuclear cells; optionally expanding these CD34+ cells; expanding these cells in the presence of cytokines that promote the differentiation of these cells to a CD34/CD36+ phenotype; and capturing or labeling the CD36+ cells of fetal origin that are present in this sample through the use of one or more of the antibodies of this invention.

The invention thus provides antibodies, preferably monoclonal antibodies, that are specific for CD36+ cells of human fetal origin. The present invention also encompasses antibody fragments, including but not limited to F(ab) and F(ab)'$_2$ fragments, of such antibodies. Antibody fragments are produced by any number of methods, including but not limited to proteolytic or chemical cleavage, chemical synthesis or preparation of such fragments by means of genetic engineering technology. The present invention also encompasses single-chain antibodies that are immunologically reactive with an epitope specific for a cell of fetal cell origin, made by methods known to those of skill in the art.

The following detailed examples are included to demonstrate preferred embodiments of the invention. It should be appreciated by those of skill in the art that the techniques disclosed in therein represent techniques that function well in the practice of the invention, and thus can be considered to constitute preferred modes for its practice. However, those of skill in the art should, in light of the present disclosure, appreciate that many changes can be made in various embodiments disclosed and still obtain a like or similar result without departing from the spirit and scope of the invention.

Example 1

Preparation of Fetal Liver Cells

Fetal liver cells were obtained from Cambrex Bio Science, Walkersville, Md.). Alternatively, such cells can be isolated from fetal livers (FL, gestational ages 15-22 weeks) from 5 different donors as follows.

Fetal livers from five donors are homogenized and passed through a wire mesh in the presence of a DPBS/0.2% BSA solution, where DPBS has a formula of $Ca^{++}/Mg^{++}$-free Dulbecco's phosphate-buffered saline (Biowhittaker, Walkersville, Md.); BSA is bovine serum albumin (Sigma St. Louis, Mo.), containing 50 µg/ml gentamicin sulfate (Life Technologies, Grand Island N.Y.). CD34+ cells can be isolated from this homogenate according to either the MACS or FACS method described in Example 3. Alternatively, this homogenate may be further purified according to the following protocol prior to CD34+ cell isolation according to either the MACS or FACS method described in Example 3

Mature erythroid cells and other Lineage positive cells are removed from the homogenate by immunomagnetic bead depletion. Briefly, the homogenate is incubated with saturating amounts of glycophorin A (GPA) mAb (American Type Culture Collection, Rockville, Md.); the cells washed twice by suspension/sedimentation in DPBS/BSA, incubated for 15 minutes with BioMag goat-mouse IgG magnetic particles (Perspective Biosystems, Framingham, Mass.); and the magnetic particle-bound GPA+ FL cells are captured by magnetic gradient separation in either a column or batch format. The GPA− FL cells, which are not bound by the magnetic microparticles, are separated from the captured cells by elution with DPBS/BSA (column) or by decantation (batch) and subjected to step density gradient separation by centrifugation for 25 minutes at 800 g (room temperature) using 1.077 g/ml Nycoprep (Life Technologies, Grand Island, N.Y.) as the dense phase. The resulting light density fetal liver (LDFL) cells are collected from the gradient interface; washed with DPBS/BSA and resuspended in 2 ml of 10 µg mouse IgG1 and IgG2a (Sigma) in DPBS/BSA to block non-specific binding of monoclonal antibodies used for further cell capture. The resulting GPA-LDFL cell suspension is incubated for 30 minutes at 4° C. with the following FITC-conjugated antibodies: anti-CD3, anti-CD4, anti-CD8, anti-CD11b, anti-CD14, anti-CD16 anti-CD19, anti-CD20, anti-CD36, anti-CD54 (comprising the Lineage panel). After washing, the labeled cells are subjected to negative selection using magnetic beads coated with sheep-anti-mouse IgG (Dynal, Oslo Norway) in the manner described above to yield GPA−Lin− LDFL cells. CD34+ cells are then isolated from the resulting GPA−Lin−

LDFL cells using the either the MACS or FACS protocol described in Example 3 below.

Example 2

Preparation of Mobilized Peripheral Blood Cells

Mobilized peripheral blood cells were obtained from Cambrex. Such cells can also be obtained as follows.

G-CSF (granulocyte colony stimulating factor) mobilized peripheral blood (MPB) mononuclear cells are obtained by leukapherisis from ten different normal adult donors and isolated according to standard protocols known to those of ordinary skill in the art. CD34$^+$ cells can be isolated from this MPB blood fraction according to either the MACS or FACS method described in Example 3. Alternatively, this MPB blood fraction can be further purified according to the following protocol prior to CD34$^+$ cell isolation according to either the MACS or FACS method described in Example 3.

The mononuclear cell fraction is depleted of mature erythroid cells and other Lineage positive cells by immunomagnetic bead depletion as described in Example 1. Briefly, mature erythroid cells and other Lineage positive cells are removed from the MPB blood fraction by incubating the cells with saturating amounts of glycophorin A (GPA) mAb; washing twice by suspension/sedimentation in DPBS/BSA; incubation for 15 minutes with BioMag goat-mouse IgG magnetic particles (Perspective Biosystems); and separating the magnetic particle bound GPA$^+$ MPB cells from the unbound GPA MPB by magnetic gradient separation in either a column or batch format. The GPA MPB cells are subjected to step density gradient separation by centrifugation for 25 minutes at 800 g (room temperature) using 1.077 g/ml Nycoprep (Life Technologies, Grand Island, N.Y.) as the dense phase. The resulting light density MPB cells are collected from the gradient interface; washed with DPBS/BSA and resuspended in 2 ml DPBS/SBA supplemented with 10 µg mouse IgG1 and IgG2a (Sigma) to block non-specific binding of monoclonal antibodies used for further cell capture. The resulting GPA-MPB cell suspension is incubated for 30 minutes at 4° C. with the following FITC conjugated antibodies: anti-CD3, anti-CD4, anti-CD8, anti-CD11b, anti-CD14, anti-CD16 anti-CD19, anti-CD20, anti-CD36, anti-CD54 (comprising the Lineage panel). After washing, the labeled cells are subjected to negative selection using magnetic beads coated with sheep-anti-mouse IgG (Dynal, Oslo Norway) in the manner described in Example 1 above to yield GPA$^-$Lin$^-$ MPB cells. CD34$^+$ cells are then isolated from the resulting GPA$^-$Lin$^-$ MPB cells using the either the MACS or FACS protocol described in Example 3 below.

Example 3

Purification of Adult and Fetal CD34$^+$ Progenitor Cells

The fetal liver cells and MPB mononuclear cell fractions of Examples 1 and 2, respectively, were enriched in CD34$^+$ cells in accordance with either of the following protocols:

MACS Protocol

The fetal liver cells and MPB mononuclear cell fractions prepared as described in Examples 1 and 2, respectively, were immunomagnetically enriched in CD34$^+$ cells using a MACS CD34 Isolation Kit (Miltenyi Biotec, Auburn, Calif.) in accordance with the manufacturer's instructions. Briefly, the mononuclear cells were incubated with hapten-labeled anti-CD34 antibody (QBEND-10, BD Pharmingen, San Diego, Calif.) in the presence of 0.1% human IgG (Bayer Elkhart, Ind.) as a blocking reagent and then incubated with anti-hapten coupled to MACS microbeads. The labeled cells were filtered through a 30 µm nylon mesh to remove cell clumps and aggregates. The labeled CD34$^+$ cells were then captured from the mixture using a high-gradient magnetic separation column (Miltenyi Biotec). After elution of the non-labeled CD34$^-$ cells, the magnetic field was removed and the magnetically retained CD34$^+$ cells were eluted from the column with staining buffer SB (DPBS supplemented with 0.2% BSA and 2 mM EDTA, pH 7.2) at 4-8° C. Greater than 90% of the recovered cells were CD34$^+$ as determined by FACS (FACSCalibur; Becton Dickinson San Jose Calif.) analysis using the CellQuest Analysis Software (Becton Dickinson).

FACS Protocol

The fetal liver and mononuclear cell fractions prepared as described in Examples 1 and 2, respectively, were alternatively enriched in CD34$^+$ cells by Fluorescence Activated Cell Sorting (FACS). The fetal liver and mononuclear cell fractions were stained with 20 µl of fluorescein-labeled anti-CD34 monoclonal antibody (catalog #34374X; BD Pharmingen) per 1×10$^6$ cells in SB for one hour at 4-8° C. Non-specific binding control cells were stained in an identical manner with fluorescein-labeled isotype-matched murine IgG$_1$ (catalog #554679; BD Pharmingen). Immediately prior to sorting, 1 µg/mL of the fluorescent DNA stain propidium iodide (PI) was added to each sample to permit identification and exclusion of nonviable cells. Cells were sorted and analyzed on a FACSVantage cell sorter (Becton Dickinson) in accordance with the manufacturer's instructions. A 488 nm argon ion laser was used for excitation of the fluorophores, and fluorescence was detected at 525 nm (fluorescein) and 620 nm (PI). Viable CD34$^+$ cells (CD34$^+$/PI$^-$) were collected and stored on ice until used. Sample cells exhibiting CD34 fluorescence intensities greater than the 99$^{th}$ percentile of those exhibited by the isotype-matched irrelevant murine IgG$_1$ controls were selected as being CD34$^+$. Forward and side light scatter excluded cell aggregates or debris. Greater than 90% of the recovered cells were CD34$^+$ as determined by FACSCalibur (Becton Dickinson) analysis using the CellQuest Analysis Software (Becton Dickinson).

Example 4

Stimulation of Fetal CD34$^+$ Cells to Express CD36

Fetal and adult CD34$^+$ cells were isolated and purified as described in Example 3 and expanded by one of two methods. In one set of experiments, CD34$^+$ cells were expanded using Hematopoietic Progenitor Growth Media (HPGM; Biowhittaker) supplemented with 50 ng/ml Flt-3 ligand (FLT-3), 100 ng/ml TPO (thrombopoietin), and 100 ng/ml SCF (stem cell factor) for from four to six days at 37° C. under 5% CO$_2$ in liquid culture. These cells were then stimulated to express CD36 by further expansion in HPGM supplemented with 3 U/ml EPO (erythropoietin), 25 ng/ml SCF, 10 ng/ml Interleukin-3 (IL-3), and 10 ng/ml Interleukin-6 (IL-6) for from four to six days at 37° C. under 5% CO$_2$. Alternatively, CD34$^+$ cells were expanded using HPGM supplemented (known hereinafter as "supplemented HPGM") with 2% deionized bovine serum albumin, 150 µg/ml iron saturated human transferring, 900 µg/ml ferrous sulfate, 90 µg/ml ferric nitrate, 100 µg/ml insulin, 30 µg/ml soybean lecithin, and 7.5 µg/ml cholesterol and 1×10$^{-6}$ M hydrocortisone (Sigma) wherein cells are cultured in supplemented HPGM containing 50 ng/ml Flt-3 ligand (FLT-3), 100 ng/ml TPO (thrombopoietin), and 100 ng/ml SCF (stem cell factor) for four to six days at 37° C.

under 5% $CO_2$ in liquid culture. These cells were then stimulated to express CD36 by further expansion in supplemented HPGM containing with 3 U/ml EPO (erythropoietin), 50 ng/ml IGF-1 (Insulin-like growth factor-1), and 50 ng/ml SCF for from four to six days at 37° C. under 5% $CO_2$. The CD36-expressing cells were recovered and purified by MACS to greater than 85% purity as determined by FACS-Calibur (Becton Dickinson) analysis using the CellQuest Analysis Software (Becton Dickinson).

Example 5

Isolation of Total RNA

Total RNA was separately isolated from the $CD36^+$ adult MPB and fetal liver cells using Trizol (Life Technologies, Gaithersburg, Md.) according to the manufacturer's instructions. Cells were pelleted and then lysed by resuspension in 1 mL Trizol per $5\times10^6$ cells by repeated pipetting. The cell lysate was then incubated for 5 minutes at room temperature and extracted with 0.2 volumes chloroform by vortexing for 1 minute. The sample was then centrifuged for 30 minutes at 13,000 rpm (12,000 g) at 4° C. in a microcentrifuge. The RNA was precipitated by the addition of 2 volumes isopropanol, mixed and allowed to sit at room temperature for 10 minutes. The RNA was centrifuged for 45 minutes at 12 000×g. The RNA pellet was washed with 75% ethanol, briefly dried; resuspended in RNase-free water or diethyl pyrocarbonate-treated (DEPC; Sigma) water (0.1%) and treated with RNase-free DNase I enzyme (Life Technologies) according to the manufacturer's instructions. The RNA concentration was then determined by using a Beckman DU 650 spectrophotometer (Beckman Instruments, Palo Alto, Calif.). Alternatively, the total RNA was isolated using the RNeasy RNA Isolation Kit (Qiagen, Valencia, Calif.) according to manufacturer's instructions.

Example 6

Preparation of cDNA for Microarray Analysis cDNA for analysis on an Affymetrix GeneChip™ microarray was prepared according to the manufacturer's instructions as set forth in the GeneChip Expression Analysis Technical Manual (Affymetrix, Santa Clara, Calif.). Briefly, total RNA was isolated from adult MPB and fetal liver cells as described in Example 4 and reverse transcribed using a T7-Oligo(dT) Promoter Primer in the first-strand cDNA synthesis reaction. The second-strand cDNA was synthesized in an RNAse-H-mediated reaction and the resulting double-stranded cDNA purified. The purified double-stranded cDNA was transcribed in the presence of T7 RNA Polymerase and a mixture of biotinylated nucleotide analogs and ribonucleotides to prepare complementary RNA (cRNA). The cRNA was fragmented and hybridized to Affymetrix U133 arrays as described in Example 7.

Example 7 cDNA Microarray Analysis

The resulting fetal and adult cDNA preparations were separately analyzed using Affymetrix U133 microarray chips according to the manufacturer's instructions. The corrected fluorescent intensities for the corresponding genes on the fetal and adult microarray chips were measured and converted to p-values in accordance with standard methods (see, Statistical Algorithms Reference Guide, Affymetrix Inc. Santa Clara, Calif.). Genes and Expressed Sequence Tags (EST) that were more strongly expressed in the fetal cDNA samples (where the Wilcoxon's Signed Ranked Test p-value (please see Genechip Expression Analysis Technical Manual for complete explanation) was greater or equal to 0.99, preferably >0.999 and more preferably 0.9999 were taken as being uniquely expressed by $CD36^+$ fetal cells relative to $CD36^+$ adult cells. The genes that are preferentially expressed in fetal CD36+ cells prepared in accordance with the present invention are listed in Table 1. The ESTs that are preferentially expressed in fetal CD36+ cells prepared in accordance with the present invention are listed in Table 2.

TABLE 1

Genes that are Preferentially Expressed by $CD36^+$ Fetal Liver Cells

| Gene name (Genbank/Unigene Accession No.) | FL/MPB signal ratio | Wilcoxon Ranked p value |
|---|---|---|
| AD037 (AI890191) | 1976/9.1 | 0.99998 |
| CSPG2 (NM_004385) | 1959.5/29.4 | 0.99998 |
| DCNP1 (Hs. 152477) | 968.6/86.7 | 0.99998 |
| Homo sapiens cDNA FLJ30298 fis, clone BRACE2003172 (AK025198.1) | 700.5/2.8 | 0.99998 |
| Homo sapiens cDNA FLJ33028 fis, clone THYMU2000140 (AL048542) | 2228.3/7.4 | 0.99998 |
| Homo sapiens cDNA: FLJ21545 fis, clone COL06195 (AK025198.1) | 4129.6/21 | 0.99998 |
| KCNJ2 (AF153820) | 244.6/18.2 | 0.99998 |
| MRC1 (NM_002438) | 2036.7/23.1 | 0.99998 |
| MS4A4A (NM_024021) | 126.9/7.9 | 0.99998 |
| MS4A6A (NM_022349) | 5229.9/44.5 | 0.99998 |
| MS4A7 (Hs.530735) | 2661.9/60.7 | 0.99998 |
| NMES1 (AF228422.1) | 116.9/10.1 | 0.99998 |
| PAG (NM_018440.1) | 981/96.2 | 0.99998 |
| PARVG (AF237772.1) | 701/17.2 | 0.99998 |
| S100A8 (AW238654) | 7132.9/31.3 | 0.99998 |
| S100A9 (NM_002965) | 2518/15 | 0.99998 |
| ASGR2 (NM_001181) | 1274.2/4.8 | 0.99998 |
| C1QG (AI184968) | 1399.7/6.1 | 0.99998 |
| TIM3 (AW025572) | 415.17/18.8 | 0.99998 |
| HRB2 (Hs. 205558) | 1064.6/59.9 | 0.99997 |
| PKIB (Hs. 486354) | 339.8/5.4 | 0.99997 |
| MAFB (Hs. 169487) | 797.4/81.3 | 0.99996 |
| MGC21854 (AI659418) | 911.1/148.9 | 0.99996 |
| PRAM-1 (Hs. 465812) | 276.6/15.8 | 0.99996 |
| AKNA (Hs. 494895) | 661.1/37.7 | 0.99992 |
| AD026 (AF226731.1) | 198.3/10.3 | 0.99990 |
| GPR84 (AF237762.1) | 411/21.3 | 0.99985 |
| JDP2 (Hs. 196482) | 875/12.5 | 0.99985 |
| RCP (BE544375) | 145.9/13.4 | 0.99969 |
| RASGRP4 (Hs. 130434) | 493.9/20.9 | 0.99956 |
| PTGFRN (Hs. 418093) | 137.8/20 | 0.99817 |
| CXCL16 (Hs. 82407) | 327.4/76.6 | 0.99775 |
| CREM (Hs. 200250) | 241.4/21.4 | 0.99751 |
| MS4A5 (Hs.178066) | Data Not Available | |
| MS4A10 (Hs.450640) | Data Not Available | |

TABLE 2

ESTs that are Preferentially Expressed by $CD36^+$ Fetal Liver Cells

| EST WITH GENBANK ACCESSION NUMBER | FL/MPB signal ratio | p value |
|---|---|---|
| AL039884 | 740.5/35.5 | 0.99998 |
| AV646597 | 1612.5/63.5 | 0.99998 |
| AW135176 | 1820/77.8 | 0.99998 |
| AW872374 | 699.2/37.9 | 0.99998 |
| BF892532 | 322.6/8.6 | 0.99998 |
| AI536637 | 288.8/9.9 | 0.99998 |

TABLE 2-continued

ESTs that are Preferentially Expressed by CD36+ Fetal Liver Cells

| EST WITH GENBANK ACCESSION NUMBER | FL/MPB signal ratio | p value |
|---|---|---|
| BE549540 | 766.7/34.4 | 0.99998 |
| AW303397 | 695.4/14.4 | 0.99997 |
| AI741439 | 221.6/7.9 | 0.99994 |
| AV660825 | 102.2/3.8 | 0.99992 |
| AI681260 | 183.9/3.6 | 0.99990 |
| AW006441 | 611/13.4 | 0.99990 |
| AW575863 | 374.4/10.4 | 0.99990 |
| AI915629 | 113/4.4 | 0.99951 |
| AA988769 | 94/2.6 | 0.99914 |
| AV688087 | 279.5/9.4 | 0.99914 |

TABLE 3

Amino Acid Sequences of Unique Peptides Corresponding to Selected Genes

| Gene | Peptide A | Peptide B |
|---|---|---|
| MS4A10 | NTTQPKLLAPHQHEKSQKKS (SEQ ID NO. 1) | CINALSSNLKSPRLSQPAEE (SEQ ID NO. 2) |
| MS4A7 | FTPKGITIPQREKPGHMYQN (SEQ ID NO. 3) | YSNNPGSSFSSTQSQDHIQQ (SEQ ID NO. 4) |
| MS4A6A | FSQAEKPEPTNQGQDSLKKH (SEQ ID NO. 5) | PASLQCELDKNNIPTRSYVS (SEQ ID NO. 6) |
| ASGR2 | HELGGSEDCVEVQPDGRWND (SEQ ID NO. 7) | LQVYRWVCEKRRNATGEVA (SEQ ID NO. 8) |
| MS4A5 | MDSSTAHSPVFLVFPPEITA (SEQ ID NO. 9) | TFGFILDQNYICGYSHQNSQ (SEQ ID NO. 10) |

Example 8

Antibody Production

The amino acid sequences of the proteins corresponding to the genes and EST's identified in Example 7 were determined by reference to GenBank, SwissProt and other publicly available sources. Each of these amino acid sequences was evaluated to identify peptide regions within each protein that had unique amino acid sequences. Where possible, two or more such peptide regions were identified for each protein. By way of example, the amino acid sequences of two unique peptide regions of the proteins encoded by the genes MS4A10, MS4A7, MS4A6A, ASGR2, MS4A5 are listed in Table 3.

A N-terminal cysteine residue was added to the MS4A10 (SEQ ID NO. 11/12), MS4A7 (SEQ ID NO. 13/14) and MS4A6A (SEQ ID NO. 15/16) peptides and the dipeptide CYS-ALA was added to the C-terminal of the MS4A5 (SEQ ID NO. 17/18) peptides to facilitate conjugation of these peptides to Keyhole Limpet Hemocyanin during the preparation of the immunogen.

These peptides were synthesized using conventional methods and polyclonal antisera and purified rabbit polyclonal antibodies were obtained from Bethel Labs, Montgomery, Tex.; said antisera and purified antibodies can be produced from said polyclonal antisera using methods that are well known to those skilled in the art (see, for example, Harlow & Lane, 1988, Antibodies: A Laboratory Manual, Cold Spring Harbor Laboratory Press: New York). The resulting antibodies were affinity purified and conjugated to the hapten biotin or the fluorophore fluorescein or phycoerythrin (PE) depending upon the intended use of the antibody conjugate thus produced.

Example 9

Isolation of CD34+ Cells from Maternal Peripheral Blood

Peripheral blood (PB) samples were obtained in heparinized collection tubes by venipuncture of pregnant female donors who were known by an independent means such as amniocentesis to be carrying a male fetus. The Y-chromosome of the fetus provided a definitive means of differentiating between otherwise identical cells of maternal and fetal origins. The collected peripheral blood was diluted with DPBS, underlaid with Ficoll-Paque (Pharmacia AB) and centrifuged at 800 g for 30 minutes at 20° C. The mononuclear cell fraction was collected from the buffy coat and were stained with 20 μl/$10^6$ cells of fluorescein-labeled anti-CD34 monoclonal antibody (catalog #34374X; BD Pharmingen) in SB for one hour at 4-8° C. Immediately prior to sorting, 1 μg/mL of the fluorescent DNA stain PI was added to each sample to permit identification and exclusion of nonviable cells. Cells were sorted and analyzed on a FACSVantage cell sorter (Becton Dickinson) in accordance with the manufacturer's instructions. A 488 nm argon ion laser was used for excitation of the fluorophores while detection was at 525 nm (fluorescein) and 620 nm (PI). Alternatively, cells were processed following the MACS protocol as described in Example 3. The CD34+ sub-population (viable CD34+ cells) was collected and stored on ice until used. By these methods, between 500 to 3000 viable CD34+ cells could typically be obtained from an approximately 30 ml sample of whole blood from a female donor, which is about 70-85% of the number of CD34+ cells expected from such a sample.

Example 10

Stimulation of CD36 Expression by CD34+ Cells from Maternal Peripheral Blood

The CD34+ cells isolated as described in Example 9 were expanded either in Hematopoietic Progenitor Growth Media (HPGM; Biowhittaker) supplemented with either 3 U/ml EPO (erythropoietin), 25 ng/ml SCF, 10 ng/ml Interleukin-3 (IL-3), and 10 ng/ml Interleukin-6 (IL-6) for three to six days at 37° C. under 5% $CO_2$ or in supplemented HPGM containing 2% deionized bovine serum albumin, 150 μg/ml iron saturated human transferring, 900 μg/ml ferrous sulfate, 90 μg/ml ferric nitrate, 100 μg/ml insulin, 30 μg/ml soybean lecithin, and 7.5 μg/ml cholesterol and $1 \times 10^{-6}$ M hydrocortisone (Sigma) and further containing 50 ng/ml Flt-3 ligand (FLT-3), 100 ng/ml TPO (thrombopoietin), and 100 ng/ml SCF (stem cell factor) for four to six days at 37° C. under 5% $CO_2$ in liquid culture. These cells were then stimulated to express CD36 by further expansion in supplemented HPGM containing with 3 U/ml EPO (erythropoietin), and 50 ng/ml IGF-1 (Insulin like growth factor-1) for from four to six days at 37° C. under 5% $CO_2$ to drive the cells to express CD36

Example 11

Separation of Fetal Cells from Maternal Blood by FACS

The phenotype-shifted CD36+ cells prepared as described in Example 10 were immuno-stained with phycoerythrin (PE) conjugated anti-CD36 (BD Pharmingen) and purified polyclonal antibodies (Bethel Labs, Montgomery, Tex.) selected from among those prepared in accordance with Example 7, conjugated to either fluorescein or biotin. If a biotin conjugated antibody was used, a streptavidin-APC (allophycocyanin) (BD Pharmingen) conjugate was used as the detection reagent. All immuno-staining was performed according to standard methods at 4-8° C. in a phosphate-buffered saline (DPBS) buffer (pH 7.4) containing 0.2% BSA. Prior to antibody staining, cells were incubated with 1% Gamimune (Bayer Health Care Research Triangle Park, N.C.) for 30 minutes at 4-8° C. to block non-specific antibody binding. The immuno-stained cells were sorted and analyzed on a FACSVantage cell sorter (Becton Dickinson) in accordance with the manufacturer's instructions. A 488 nm argon ion laser was used for excitation of the fluorophores while detection was at 525 nm (fluorescein) and 575 nm (PE and APC). Those cells that stained positively for both CD36 and the target peptide were collected and stored on ice until used. Control cells were incubated with fluorochrome-conjugated isotype-matched IgM-fluorescein (BD Pharmingen), IgM-PE (BD Pharmingen) or anti-rabbit isotype controls. Cell aggregates or debris were excluded by gating on forward and side light scattering.

Example 12

Magnetic Separation of Fetal Cells from Maternal Blood

The phenotype-shifted $CD36^+$ cells prepared as described in Example 10 were immuno-stained with phycoerythrin (PE) conjugated anti-CD36 (BD Pharmingen) and a biotin-conjugated antibody selected from among those prepared in accordance with Example 7. The doubly-labeled cells were incubated with streptavidin-conjugated MACS microbeads (Miltenyi Biotec) and filtered through a 30 μm nylon mesh to remove cell clumps and aggregates. Cells expressing the selected fetal cell marker were then captured from the mixture using a high-gradient magnetic separation column according to the manufacturer's instructions. After elution of the non-retained cells, the magnetic field was removed and the magnetically retained fetal cells were eluted from the column with SB. The $CD36^+$ fetal cells in this eluate were those that were also labeled with PE. All immuno-staining was performed according to standard methods at 4-8° C. in a DPBS buffer (pH 7.4) containing 0.2% BSA.

Example 13

Detection of Gene Expression Using RNA Probes

Fetal cell expression of the genes identified in Example 7 is demonstrated using RNA probes. Briefly, RNA templates corresponding to one or more of the genes identified as described in Example 7 are prepared according to the protocol provided using the Promega T-7 Riboprobe In-vitro Transcription System (Promega, Madison, Wis.) in accordance with its instructions or can be purchased inter alia from GeneDetect.com (Auckland, NZ). 5'-($\alpha^{35}$S)rUTP can be obtained from Amersham Pharmacia Biotech (Piscataway, N.J.) or NEN/Perkin Elmer (Boston, Mass.). All other reagents can be obtained from Promega unless otherwise noted. Buffers are prepared in accordance with the instructions provided for the GeneDetect One-Step RNA Probe Synthesis Templates unless otherwise specified.

RNA Probe Preparation

RNA probes are prepared as follows. Two μl of 5× Transcription Buffer, 1 μl of 100 mM dithiothreitol (DTT), 1 μL of RNAsin RNAse inhibitor; 1 μg of the desired RNA template(s) in 3 μl water; and a mixture containing 5 μM each of GTP, CTP and ATP in 2 μl of Transcription Buffer is added to 25 μl of $^{35}$S-UTP lyophilized into the bottom of a 1.5 mL microfuge tube. After mixing, 1 μl of T7 RNA Polymerase is added to the mixture, mixed and incubated for one hour at 30° C. To ensure complete transcription, a second 1 μl aliquot of T7 RNA Polymerase is added to the mixture, mixed and incubated for an additional one hour at 30° C. before stopping the reaction by the addition of 1 μl of RQ1 Dnase and incubating for 15 minutes at 37° C. The RNA probe is recovered from the reaction mixture by the addition of 20 μl of 10 mM Tris-HCl/1 mM EDTA (pH 8.0) buffer (TE) and 50 μg of tRNA; vortexing; and desalting on a G-50 Sephadex column (Amersham Pharmacia Biotech). Probe integrity is confirmed by electrophoresis on a 15% polyacrylamide gel in Tris-Borate-EDTA (TBE)-Urea buffer.

Fetal Cell Staining Using RNA Probes $CD36^+$/peptide$^+$ cells collected by FACS as described in Example 11 or by magnetic separation as described in Example 12 are prepared as monolayer cellular preparations on a glass microscope slide by settling, CytoSpin (Thermo-Shandon, Pittsburgh, Pa.), ThinPrep (Cytyc, Boxborough, Mass.) or similar standard method. The cells are covered with 100 μl of hybridization buffer (HB) and incubated at 42° C. for 1-3 hours to permeabilize the cells. For each slide to be processed, 2 μl of the desired RNA probe and 1 μl of 50 mg/mL tRNA are combined, heated to 95° C. for 3 minutes and cooled by the addition of 17 μl of HB. 20 μl of the resulting mixture added to the 100 μl droplet of HB on the slide and incubated overnight at 45-55° C. The labeled specimens are then washed twice for 10 minutes each with 2×SSC-BME-EDTA at room temperature; immersed in a 20 mg/ml solution of RNAse A for 30 minutes at room temperature; washed twice for 10 minutes each with 2×SSC-BME-EDTA at room temperature; washed for 2 hours with 4 L of 0.1× SSC-MBE-EDTA; washed 2×10 minutes in 0.5×SSC at room temperature; dehydrated for 2 minutes each in 50%, 70% and 90% ethanol containing 0.3M ammonium acetate and dried in a vacuum desiccator. Labeled cells are detected by autoradiography in the standard manner.

Example 14

Diagnostic Testing of Fetal Cells

Microscopic Detection and Evaluation of Fetal Cells Isolated from Maternal Blood.

$CD36^+$/peptide$^+$ cells that can be collected by FACS as described in Example 11 or by magnetic separation as described in Example 12 are prepared as monolayer cellular preparations on a glass microscope slide by undisturbed settling, CytoSpin (Thermo-Shandon, Pittsburgh, Pa.), Thin-Prep (Cytyc, Boxborough, Mass.) or similar method, immuno-stained as previously described; and evaluated using fluorescence microscopy in accordance with methods known to those skilled in the art. The presence of cells that stain positively for both CD36 and the target peptide is indicative of the presence of fetal cells in the preparation. The preparation may be subsequently counterstained in-situ with a chromatic stain such as hemotoxylin and the cells therein evaluated morphologically or subjected to an in-situ hybridization staining method such as fluorescence in situ hybridization (FISH) to detect the presence of specific genes or mutated genes within the cells in the preparation. Such counterstainings are performed according to procedures that are known to those skilled in the art. If the physical locations of the CD36+/peptide+ cells within the preparation are determined, this location information can be used to correlate the results obtained by morphological analysis or in-situ hybridization with specific fetal cells in the preparation. Such correlations between CD36+/peptide+ cells and the same cells subsequently stained with additional reagents can readily be performed using commercially available automated microscopy systems such as exemplified by the AcCell or TracCell computer assisted microscopy systems (Molecular Diagnostics, Chicago, Ill.).

Example 15

Diagnostic Testing of Fetal Cells

PCR

Detection of the Y-Chromosome in Cells from a Male Fetus Isolated from Maternal Blood.

The CD36+/peptide+ cells collected by FACS as described in Example 11 were tested by PCR to determine whether they contained a Y-chromosome. Briefly, whole genomic DNA was extracted from isolated cells by modified salt precipitation method (Puregene DNA Isolation Kit, Gentra systems, Minneapolis, Minn.). Approximately 50-200 ng of DNA was analyzed by conventional Polymerase Chain Reaction (PCR) for both the GAPDH and SRY loci, using a GeneAmp PCR system 9700 Thermocycler (Perkin Elmer, Foster City, Calif.), Platinum Taq DNA Polymerase (Invitrogen Corporation, Carlsbad, Calif.) as an enzyme, and the following procedure. Thin-walled PCR micro-tubes were first incubated at 94° C. for 2 minutes to denature the sample and activate the enzyme. Samples were then subjected to 10 cycles of amplification (the first 5 cycles consisting of a 15 seconds denaturation step at 94° C., 30 second annealing step at 59° C., with the subsequent 5 cycles consisting of a 15 second denaturation step at 94° C., 30 second annealing step at 57° C.) followed by 30 cycles consisting of a 15 second denaturation step at 94° C., 30 second annealing step at 55° C.). This was followed by a final extension step for 10 minutes at 72° C. The SRY sequence was used to measure the presence of fetal DNA, while the glyceraldehyde-3-phosphate dehydrogenase (GAPDH) sequence was used to confirm the integrity and quality of DNA in each sample. The following oligonucleotides were used: SRY forward 5'-TCC TCA AAA GAA ACC GTG CAT-3' (SEQ ID NO. 19), SRY reverse 5'-AGA TTA ATG GTT GCT AAG GAC TGG AT-3' (SEQ ID NO. 20), GAPDH forward 5'-CCC CAC ACA CAT GCA CTT ACC-3' (SEQ ID NO. 21) and GAPDH reverse 5'-CCT AGT CCC AGG GCT TTG ATT-3' (SEQ ID NO. 22). The PCR products were separated by 2% agarose gel electrophoresis, and the presence of a Y-chromosome specific fragment obtain from DNA from these cells demonstrated that they originated from the (male) fetus rather than from the mother. By substituting the appropriate primers for the Y-chromosome primer, PCR analysis may employed in a similar manner to detect the presence of specific genes and mutated genes in the collected cells including ones that have been correlated with the presence of particular disease states. Similarly, the collected cells may be subjected to analyses by methods such as FISH if suitable probes are employed.

Example 16

Diagnostic Testing of Fetal Cells

RT-PCR

Detection of the Y-Chromosome in Cells from a Male Fetus Isolated from Maternal Blood.

Real time quantitative PCR analysis is performed on isolated fetal cells as described in Example 11 using ABI PRISM 7700 Sequence Detection System (Applied Biosystem, Foster City, Calif.), As an internal control, the β-globin TaqMan system can be used consisting of two primers β-globin-354 (forward), 5'-GTG CAC CTG ACT CCT GAG GAG A-3' (SEQ ID NO. 23); β-globin-455 (reverse), 5'-CCT TGA TAC CAA CCT GCC CAG-3' (SEQ ID NO. 24) and a dual-labeled fluorescent TaqMan probe β-globin-402T, 5'(FAM) MG GTG AAC GTG GAT GAA GTT GGT GG (TAMRA)-3' (SEQ ID NO. 25). To detect the presence of Y chromosome in isolated fetal samples as previously described, the SRY TaqMan system can be used consisting of SRY-109 (forward) primer, 5'-TGG CGA TTA AGT CM ATT CGC-3' (SEQ ID NO. 26); SRY-245 (reverse) primer, 5'-CCC CCT AGT ACC CTG ACA ATG TAT T-3' (SEQ ID NO. 27) and a probe SRY-142T, 5'(FAM) AGC AGT AGA GCA GTC AGG GAG GCA GA (TAMRA)-3' (SEQ ID NO. 28). TaqMan amplification reactions are set up in a reaction volume of 25 µl using the TaqMan Universal PCR Master Mix (Applied Biosystems). DNA amplifications are carried out in 8-well reaction optical tubes/strips (Applied Biosystems). The TaqMan PCR conditions are used as described in TaqMan guidelines using 40 cycles of 95° C. for 15 s and 60° C. for 1 min. with 2-min preincubation at 50° C. required for optimal AmpErase UNG activity and 10-min preincubation at 95° C. required for activation of AmpliTaq Gold DNA polymerase. Each sample was analyzed in triplicate. A calibration curve is run in parallel with each analysis.

Example 17

Diagnostic Testing of Fetal Cells

FISH Determination of the Sex of a Fetus Using Fetal Cells Isolated from Maternal Blood.
Slide Preparation Cells of fetal origin isolated as described in Examples 11 or 12, respectively, are pelleted in 15 mL screw-capped tubes using a table-top centrifuge and washed once with HPGM containing 10 U/mL of heparin (ICN Biomedicals Inc, Aurora, Ohio). The cells are resuspended in 100 to 200 µL of HPGM/heparin. A PAP pen (Research Products International, Mt. Prospect, Ill.) is used to mark a rectangle on silane-treated slides, and 100 to 200 µL of cell suspension is spread throughout the rectangle. Slides are incubated for 30 to 45 minutes at room temperature (RT) to allow the cells to settle and attach to the slides. Excess liquid is removed by tipping the slides sideways and the slides air-dried. The slides are fixed with methanol:acetic acid (3:1) for 15 minutes and allowed to air-dry. Slides are stored at −80° C. until use.
Fluorescent In Situ Hybridization (FISH)

On the day of hybridization, the specimens are thawed at room temperature (RT), refixed with methanol:acetic acid (3:1), air-dried, and pretreated by incubation for 30 minutes at 37° C. in 2×SSC (3M NaCl, 0.3M sodium citrate, pH 7.0). This is followed by dehydration in a series containing ethanol at 70, 90, and 100% concentrations at RT. The specimens are then treated with pepsin (20 mg/ml, Sigma) to improve probe penetration and denatured in 70% formamide/2×SSC for 2 minutes at 72° C. followed by the dehydration series described above, on ice. 600 µl of each alpha-satellite centromere specific probe for chromosomes X and Y, 16.8 µl of CEP buffer (Vysis, Downers Grove, Ill.) and 2 µl of water are combined. The probe mixture is then denatured at 70° C. for 5 minutes and applied to prewarmed (37° C.) target specimens. The hybridization area is sealed with a glass coverslip and placed into an 80° C. oven for 90 seconds. After an overnight hybridization at 37° C. in a humidified chamber, the coverslip and glue are removed. The slide is then washed in 0.25×SSC at 67° C. for 12 seconds and rinsed in 1×PBD (2-phenyl-5-(4-biphenyl)-1,3,4-oxadiazole; ONCOR Gaithersburg, Md.) for 1 minute. The specimens are then counterstained with DAPI (4,6-diamidino-2-phenylindole II; Vysis) for 10 minutes prior to microscopic analysis. The presence of X- and Y-chromosomes is determined by fluorescence microscopy using a Zeiss Axioskop microscope (Carl Zeiss, Thornwood, N.Y.).

The descriptions of particular antibodies and methods embodied above are intended to be representative of and not limiting to the present invention. Although the antibodies and methods of this invention have been described in terms of preferred embodiments, it will be apparent to those skilled in the art that alternative implementations, compositions and/or methods herein described can be made without departing from the concept, spirit and scope of the invention. Specifically, it will be apparent that the antibodies herein described may be implemented by alternative means and that the compositions and conditions described herein may be altered for compatibility with specific cell and specimen types while still achieving the same or similar results as described herein. All such similar substitutes and modifications apparent to those skilled in the art are deemed to be within the scope and spirit of the invention as defined by the appended claims.

We claim:

1. A method for producing antibodies specific for fetal CD36+ cells, comprising the steps of:
    (a) stimulating CD34+ adult cells isolated from a biological fluid to express CD36;
    (b) isolating differentiated adult cells stimulated according to step (a);
    (c) stimulating CD34+ fetal cells isolated from fetal tissue to express CD36;
    (d) isolating differentiated fetal cells stimulated according to step (c);
    (e) isolating total RNA from the adult cells of step (b) and the fetal cells of step (d);
    (f) analyzing said isolated total RNA of step (e) to identify genes encoding cellular proteins that are significantly expressed by the isolated fetal cells, but not significantly expressed by the isolated adult cells;
    (g) obtaining cellular proteins or peptides thereof that are encoded by the genes identified in step (f); and
    (h) preparing antibodies against the cellular proteins or peptides thereof obtained in step (g) using the cellular proteins or peptides thereof as antigens.

2. The method according to claim 1, wherein the isolated CD34+ cells are incubated in the presence of the cytokines Flt-3 ligand, TPO (thrombopoietin), and SCF (stem cell factor).

3. The method according to claim 1, wherein the CD34+ cells are stimulated to express CD36 by incubating the cells in the presence of:
    (i) EPO (erythropoietin), SCF, Interleukin-3 (IL-3), and Interleukin-6 (IL-6);
    (ii) EPO, IGF-1 (Insulin-like growth factor-1), and SCF; or
    (iii) EPO, SCF, IL-3, and IGF-1.

4. The method according to claim 3, wherein the isolated CD34+ cells are incubated in the presence of hematopoietic progenitor growth media (HPGM) supplemented with 2% deionized bovine serum albumin, 150 µg/mL iron saturated human transferrin, 900 µg/mL ferrous sulfate, 90 µg/mL ferric nitrate, 100 µg/mL insulin, 30 µg/mL soybean lecithin, and 7.5 µg/mL cholesterol and $1 \times 10^{-6}$ M hydrocortisone.

5. The method according to claim 1, wherein said analyzing in step (f) comprises hybridizing cDNA prepared from the isolated total RNA from the adult cells of step (e) to a cDNA microarray and hybridizing cDNA prepared from the isolated total RNA from the fetal cells of step (e) to a cDNA microarray.

6. The method according to claim 1, wherein the biological fluid is maternal blood.

* * * * *

UNITED STATES PATENT AND TRADEMARK OFFICE
CERTIFICATE OF CORRECTION

Page 1 of 2

PATENT NO. : 8,026,054 B2
APPLICATION NO. : 11/570655
DATED : September 27, 2011
INVENTOR(S) : Arun Sharma and Sherman Elias It is certified that error appears in the above-identified patent and that said Letters Patent is hereby corrected as shown below:

In column 29, the sequence identified in field <400> SEQUENCE: 14 appears as follows:

Cys Phe Thr Pro Lys Gly Ile Thr Ile Pro Gln Arg Glu Lys Pro Gly
  1               5                   10                  15

His Met Tyr Gln Asn
              20

The sequence identified in field <400> SEQUENCE: 14 should appear as follows:

Cys Tyr Ser Asn Asn Pro Gly Ser Ser Phe Ser Ser Thr Gln Ser Gln
  1               5                   10                  15

Asp His Ile Gln Gln
              20

In column 29, the sequence identified in field <400> SEQUENCE: 17 appears as follows:

Cys Ala Met Asp Ser Ser Thr Ala His Ser Pro Val Phe Leu Val Phe
  1               5                   10                  15

Pro Pro Glu Ile Thr Ala
              20

The sequence identified in field <400> SEQUENCE: 17 should appear as follows:

Met Asp Ser Ser Thr Ala His Ser Pro Val Phe Leu Val Phe Pro Pro
  1               5                   10                  15

Glu Ile Thr Ala Cys Ala
              20

Signed and Sealed this
Eleventh Day of September, 2012

David J. Kappos
*Director of the United States Patent and Trademark Office*

CERTIFICATE OF CORRECTION (continued)
U.S. Pat. No. 8,026,054 B2

In column 29, the sequence identified in field <400> SEQUENCE: 18 appears as follows:

Cys Ala Thr Phe Gly Phe Ile Leu Asp Gln Asn Tyr Ile Cys Gly Tyr
1               5                   10                  15

Ser His Gln Asn Ser Gln
            20

The sequence identified in field <400> SEQUENCE: 18 should appear as follows:

Thr Phe Gly Phe Ile Leu Asp Gln Asn Tyr Ile Cys Gly Tyr Ser His
1               5                   10                  15

Gln Asn Ser Gln Cys Ala
            20